(12) United States Patent
Miyata et al.

(10) Patent No.: US 7,381,742 B2
(45) Date of Patent: Jun. 3, 2008

(54) OPTICALLY ACTIVE POLYMALEIMIDE DERIVATIVES AND PROCESS FOR THEIR PRODUCTION

(75) Inventors: Takuya Miyata, Yamaguchi-ken (JP); Kouji Kawabata, Yamaguchi-ken (JP); Takumi Kagawa, Yamaguchi-ken (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 11/653,373

(22) Filed: Jan. 16, 2007

(65) Prior Publication Data

US 2007/0131616 A1 Jun. 14, 2007

Related U.S. Application Data

(62) Division of application No. 10/847,289, filed on May 18, 2004, now Pat. No. 7,186,750.

(30) Foreign Application Priority Data

May 22, 2003 (JP) ............................. 2003-144793

(51) Int. Cl.
*A61K 31/40* (2006.01)
*C07D 207/444* (2006.01)
(52) U.S. Cl. ...................................... 514/428; 548/548
(58) Field of Classification Search ................ 514/428; 548/548
See application file for complete search history.

(56) References Cited

U.S. PATENT DOCUMENTS 2,964,534 A * 12/1960 Sullivan ...................... 548/433
7,186,750 B2 * 3/2007 Miyata et al. ............... 514/428
2003/0069385 A1 4/2003 Kagawa et al.

FOREIGN PATENT DOCUMENTS

EP 1 288 201 A 3/2003

OTHER PUBLICATIONS

Merck Parts Index.*

Patent Abstracts of Japan, vol. 2000, No. 21, Aug. 3, 2001 & JP 2001 106729 A, Apr. 17, 2001.
Oishi et al, "Asymmetric Anionic Polymerization of Maleimides Bearing Bulky Substituents", Journal of Polymer Science, Polymer Chemistry Edition, John Wiley and Sons, New York, vol. 38, No. 2, Jan. 15, 2000; XP000878169.
Oishi et al, "Asymmetric polymerization of N-substituted malemides with chiral oxazolidine-organolithium", J. Polym Sci Part A; Journal of Polymer Science, Part A: Polymer Chemistry Feb. 15, 1999, John Wiley & Sons Inc., New York, vol. 37, No. 4, Feb. 15, 1999; XP002291802.
Sakota et al, "Photosensitized copolymerization of optically active N-1-menthylmaleimide with styrene amd methyl methacrylate", Journal of Polymer Science, Polymer Chemistry Edition, 12(8), 1787-97; XP002291803.
Yamaguchi et al, "Preparation of Optically Active N-Bornyl Maleimide and Poly(N-Bornyl-Maleimide)", Journal of Polymer Science, Part A, Polymer Chemistry, vol. 8, No. 4, 1970, pp. 929-941; XP002291804.
Booker-Milburn, et al, "Intramolecular Photocycloaddition of N-Alkenyl Substituted Maleimides," Eur. J. Org. Chem., 2001, 1473-1482.

* cited by examiner

*Primary Examiner*—Joseph McKane
*Assistant Examiner*—Susannah Chung
(74) *Attorney, Agent, or Firm*—Nixon & Vanderhye P.C.

(57) ABSTRACT

Optically active maleimide derivatives of the formula:

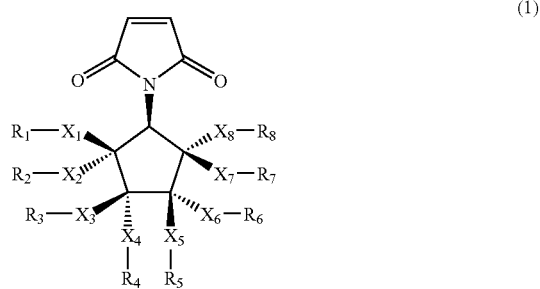

(1)

(where the various substituents are as defined in the description) are used as separating media for separating optical isomers and geometrical isomers such as by high performance liquid chromatography.

6 Claims, No Drawings

OPTICALLY ACTIVE POLYMALEIMIDE DERIVATIVES AND PROCESS FOR THEIR PRODUCTION

This application is a divisional of application Ser. No. 10/847,289 filed May 18, 2004, which claims priority of Japanese application Ser. No. 2003-144793 filed May 22 2003, the entire contents of each of which are hereby incorporated by reference in this application.

The present invention relates to a novel optically active maleimide derivative, an optically active polymaleimide derivative, a process for its production and its use. Optically active maleimide derivatives are expected to be useful for, e.g., separating media for optical isomers and geometrical isomers.

Numbers of optically active synthetic polymers are known to be useful as resolving media for optical isomers, and they include optically active triphenylmethyl methacrylate polymers (JP-A-56-106907), optically active acrylamide polymers (JP-A-56-167708) and polyacrylamides having an optically active pendant group chemically bonded to the surface of silica gel (JP-A-63-14446).

These optically active polymers have excellent resolving power for certain compounds but can resolve only limited racemates. Novel types of polymer compounds having specific performance are needed to broaden their applications.

Besides, the advancement of analytical techniques and instruments has created a desire for separating media with higher resolving power.

In view of the above-mentioned problems, the present inventors already filed a patent application for optically active poly(N-1-cyclohexyl-1-maleimide) derivatives (JP-A-2003-64054).

As described above, separation of various racemates requires numbers of novel polymer compounds having specific performance, and development of these novel compounds and separating media comprising them has been strongly desired.

The present invention was accomplished in view of the above-mentioned problems and is aimed at providing novel separating media for optical isomers having high resolving power.

The present inventors conducted extensive studies to develop separating media for optical isomers having high resolving power and, as a result, have found a novel optically active maleimide derivative represented by the following formula (1), a novel optically active polymaleimide derivative represented by the following formula (3) obtained by asymmetric anionic polymerization of the maleimide derivative and usefulness of the polymaleimide derivative as separating media for optical isomers. The present invention has been accomplished on the basis of the discovery.

Namely, the present invention provides an optically active maleimide dericative represented by the following formula (1):

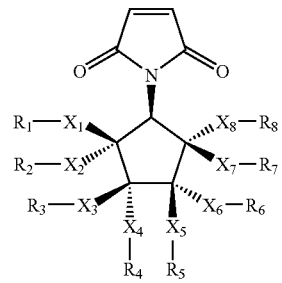

(1)

wherein each of $X_1$ to $X_8$ is independently a methylene group, an oxygen atom, a carbonyl group, a carbonyloxy group, a carbonylamino group, an aminocarbonyl group, an aminocarbonyloxy group or a single bond, and each of $R_1$ to $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group, provided that not all of $R_1$—$X_1$, $R_2$—$X_2$, $R_3$—$X_3$, $R_4$—$X_4$, $R_5$—$X_5$, $R_6$—$X_6$, $R_7$—$X_7$ and $R_8X_8$ are the same substituents;

a process for producing an optically active maleimide derivative, which comprises reacting an optically active cyclopentylamine derivative represented by the following formula (2) with maleic acid:

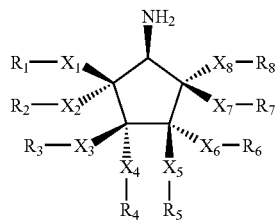

(2)

wherein each of $X_1$ to $X_8$ is independently a methylene group, an oxygen atom, a carbonyl group, a carbonyloxy group, a carbonylamino group, an aminocarbonyl group, an aminocarbonyloxy group or a single bond, and each of $R_1$ to $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group, provided that not all of $R_1$—$X_1$, $R_2$—$X_2$, $R_3$—$X_3$, $R_4$—$X_4$, $R_5$—$X_5$, $R_6$—$X_6$, $R_7$—$X_7$ and $R_8$—$X_8$ are the same substituents;

an optically active polymaleimide derivative represented by the following formula (3):

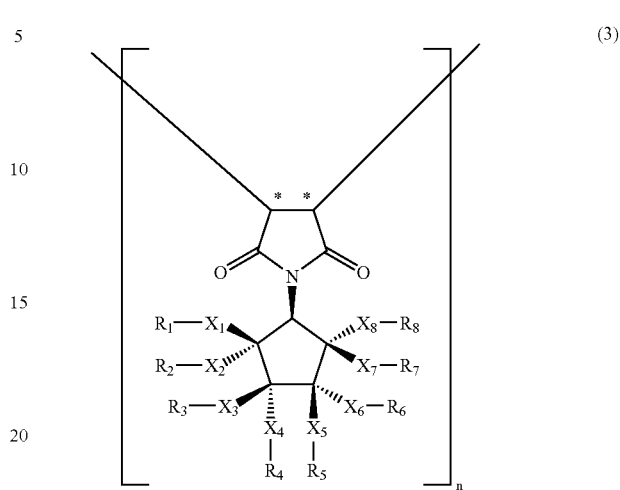

(3)

wherein each of $X_1$ to $X_8$ is independently a methylene group, an oxygen atom, a carbonyl group, a carbonyloxy group, a carbonylamino group, an aminocarbonyl group, an aminocarbonyloxy group or a single bond, each of $R_1$ to $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group, provided that not all of $R_1$—$X_1$, $R_2$—$X_2$, $R_3$—$X_3$, $R_4$—$X_4$, $R_5$—$X_5$, $R_6$—$X_6$, $R_7$—$X_7$ and $R_8$—$X_8$ are the same substituents, n is from 2 to 10000, and * indicates asymmetric carbon;

a process for producing the optically active polymaleimide derivative represented by the above formula (3), which comprises asymmetric anionic polymerization of the optically active maleimide derivative represented by the above formula (1);

a separating medium consisting of the optically active polymaleimide derivative represented by the above formula (3);

a separating medium comprising the optically active polymaleimide derivative represented by the above formula (3) and a supporting the optically active polymaleimide derivative;

a packed column for chromatography which comprises a column and the optically active polymaleimide derivative packed in the column;

a method for separating an optically active compound, which uses the separating medium; and a method for separating an optically active compound, which comprises separating an optically active compound by high performance liquid chromatography using the packed column.

Now, the present invention will be described in detail.

The optically active maleimide derivative of the present invention is a compound represented by the above formula (1).

In the above formula (1), it is preferred that $R_3$—$X_3$, $R_4$—$X_4$, $R_5$—$X_5$ and $R_6$—$X_6$ are hydrogen atoms, each of $X_1$, $X_2$, $X_7$ and $X_8$ is independently a methylene group, an oxygen atom, a carbonyl group, a carbonyloxy group, a carbonylamino group, an aminocarbonyl group, an aminocarbonyloxy group or a single bond, and each of $R_1$, $R_2$, $R_7$ and $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group (provided that not all of $R_1$—$X_1$, $R_2$—$X_2$, $R_7$—$X_7$ and $R_8$—$X_8$ are the same substituents).

In the above formula (1), it is particularly preferred that $R_3$—$X_3$, $R_4$—$X_4$, $R_5$—$X_5$ and $R_6$—$X_6$ are hydrogen atoms, each of $X_1$, $X_2$, $X_7$ and $X_8$ is independently an oxygen atom or a single bond, and each of $R_1$, $R_2$, $R_7$ and $R_8$ is independently a hydrogen atom, a $C_{5-10}$ aromatic group, a benzyl group or a 2-phenylethyl group (provided that not all of $R_1$—$X_1$, $R_2$—$X_2$, $R_7$—$X_7$ and $R_8$—$X_8$ are the same substituents).

As specific examples of the optically active maleimide derivative of the present invention represented by the above formula (1), compounds having one substituent at the 2-, 3-, 4- or 5-position of the cyclopentyl group include, for example, N-[(1S,2S)-2-methylcyclopentyl]maleimide, N-[(1S,2S)-2-ethylcyclopentyl]maleimide, N-[(1S,2S)-2-n-propylcyclopentyl]maleimide, N-[(1S,2S)-2-i-propylcyclopentyl]maleimide, N-[(1S,2S)-2-n-butylcyclopentyl]maleimide, N-[(1S,2S)-2-i-butylcyclopentyl]maleimide, N-[(1S,2S)-2-t-butylcyclopentyl]maleimide, N-[(1S,2S)-2-phenylcyclopentyl]maleimide, N-[(1S,2S)-2-benzylcyclopentyl]maleimide, N-[(1S,2S)-2-(2-phenylethyl)cyclopentyl]maleimide, N-[(1S,2S)-2-methoxycyclopentyl]maleimide, N-[(1S,2S)-2-ethoxycyclopentyl]maleimide, N-[(1S,2S)-2-n-propoxycyclopentyl]maleimide, N-[(1S,2S)-2-i-propoxycyclopentyl]maleimide, N-[(1S,2S)-2-n-butoxycyclopentyl]maleimide, N-[(1S,2S)-2-i-butoxycyclopentyl]maleimide, N-[(1S,2S)-2-t-butoxycyclopentyl]maleimide, N-[(1S,2S)-2-phenoxycyclopentyl]maleimide, N-[(1S,2S)-2-benzyloxycyclopentyl]maleimide, N-[(1S,2S)-2-(2-phenylethoxy)cyclopentyl]maleimide, N-[(1S,2S)-2-acetylcyclopentyl]maleimide, N-[(1S,2S)-2-propionylcyclopentyl]maleimide, N-[(1S,2S)-2-n-butyrylcyclopentyl]maleimide, N-[(1S,2S)-2-i-butyrylcyclopentyl]maleimide, N-[(1S,2S)-2-n-valerylcyclopentyl]maleimide, N-[(1S,2S)-2-i-valerylcyclopentyl]maleimide, N-[(1S,2S)-2-pivaloylcyclopentyl]maleimide, N-[(1S,2S)-2-benzoylcyclopentyl]maleimide, N-[(1S,2S)-2-phenylacetylcyclopentyl]maleimide, N-[(1S,2S)-2-(3-phenylpropionyl)cyclopentyl]maleimide, N-[(1S,2S)-2-acetoxycyclopentyl]maleimide, N-[(1S,2S)-2-propionyloxycyclopentyl]maleimide, N-[(1S,2S)-2-n-butyryloxycyclopentyl]maleimide, N-[(1S,2S)-2-i-butyryloxycyclopentyl]maleimide, N-[(1S,2S)-2-n-valeryloxycyclopentyl]maleimide, N-[(1S,2S)-2-i-valeryloxycyclopentyl]maleimide, N-[(1S,2S)-2-pivaloyloxycyclopentyl]maleimide, N-[(1S,2S)-2-benzoyloxycyclopentyl]maleimide, N-[(1S,2S)-2-phenylacetoxycyclopentyl]maleimide, N-[(1S,2S)-2-(3-phenylpropionyloxy)cyclopentyl]maleimide, N-[(1S,2S)-2-methoxycarbonylcyclopentyl]maleimide, N-[(1S,2S)-2-ethoxycarbonylcyclopentyl]maleimide, N-[(1S,2S)-2-n-propoxycarbonylcyclopentyl]maleimide, N-[(1S,2S)-2-i-propoxycarbonylcyclopentyl]maleimide, N-[(1S,2S)-2-n-butoxycarbonylcyclopentyl]maleimide, N-[(1S,2S)-2-i-butoxycarbonylcyclopentyl]maleimide, N-[(1S,2S)-2-t-butoxycarbonylcyclopentyl]maleimide, N-[(1S,2S)-2-phenoxycarbonylcyclopentyl]maleimide, N-[(1S,2S)-2-benzyloxycarbonylcyclopentyl]maleimide, N-[(1S,2S)-2-(2-phenylethoxycarbonyl)cyclopentyl]maleimide, N-[(1S,2S)-2-N-acetylaminocyclopentyl]maleimide, N-[(1S,2S)-2-

N-propionylaminocyclopentyl]maleimide, N-[(1S,2S)-2-N-n-butyrylaminocyclopentyl]maleimide, N-[(1S,2S)-2-N-i-butyrylaminocyclopentyl]maleimide, N-[(1S,2S)-2-N-n-valerylaminocyclopentyl]maleimide, N-[(1S,2S)-2-N-i-valerylaminocyclopentyl]maleimide, N-[(1S,2S)-2-N-pivaloylaminocyclopentyl]maleimide, N-[(1S,2S)-2-N-benzoylaminocyclopentyl]maleimide, N-[(1S,2S)-2-N-phenylacetylaminocyclopentyl]maleimide, N-[(1S,2S)-2-(N-3-phenylpropionylamino)cyclopentyl]maleimide, N-[(1S,2S)-2-N-methylcarbamoylcyclopentyl]maleimide, N-[(1S,2S)-2-N-ethylcarbamoylcyclopentyl]maleimide, N-[(1S,2S)-2-N-n-propylcarbamoylcyclopentyl]maleimide, N-[(1S,2S)-2-N-i-propylcarbamoylcyclopentyl]maleimide, N-[(1S,2S)-2-N-n-butylcarbamoylcyclopentyl]maleimide, N-[(1S,2S)-2-N-i-butylcarbamoylcyclopentyl]maleimide, N-[(1S,2S)-2-N-t-butylcarbamoylcyclopentyl]maleimide, N-[(1S,2S)-2-N-phenylcarbamoylcyclopentyl]maleimide, N-[(1S,2S)-2-N-benzylcarbamoylcyclopentyl]maleimide, N-[(1S,2S)-2-(N-2-phenylethylcarbamoyl)cyclopentyl]maleimide, N-[(1S,2S)-2-N-methylcarbamoyloxycyclopentyl]maleimide, N-[(1S,2S)-2-N-ethylcarbamoyloxycyclopentyl]maleimide, N-[(1S,2S)-2-N-n-propylcarbamoyloxycyclopentyl]maleimide, N-[(1S,2S)-2-N-i-propylcarbamoyloxycyclopentyl]maleimide, N-[(1S,2S)-2-N-n-butylcarbamoyloxycyclopentyl]maleimide, N-[(1S,2S)-2-N-i-butylcarbamoyloxycyclopentyl]maleimide, N-[(1S,2S)-2-N-t-butylcarbamoyloxycyclopentyl]maleimide, N-[(1S,2S)-2-N-phenylcarbamoyloxycyclopentyl]maleimide, N-[(1S,2S)-2-N-benzylcarbamoyloxycyclopentyl]maleimide, N-[(1S,2S)-2-(N-2-phenylethylcarbamoyloxy)cyclopentyl]maleimide and the like.

Compounds having two substituents at any of the 2-, 3-, 4- and 5-positions of the cyclopentyl group include, for example, N-[(1S,2S,3S)-2,3-dimethylcyclopentyl]maleimide, N-[(1S,2S,3S)-2,3-diethylcyclopentyl]maleimide, N-[(1S,2S,3S)-2,3-di-n-propylcyclopentyl]maleimide, N-[(1S,2S,3S)-2,3-di-i-propylcyclopentyl]maleimide, N-[(1S,2S,3S)-2,3-di-n-butylcyclopentyl]maleimide, N-[(1S,2S,3S)-2,3-di-i-butylcyclopentyl]maleimide, N-[(1S,2S,3S)-2,3-di-t-butylcyclopentyl]maleimide, N-[(1S,2S,3S)-2,3-dimethoxycyclopentyl]maleimide, N-[(1S,2S,3S)-2,3-diethoxycyclopentyl]maleimide, N-[(1S,2S,3S)-2,3-di-n-propoxycyclopentyl]maleimide, N-[(1S,2S,3S)-2,3-di-i-propoxycyclopentyl]maleimide, N-[(1S,2S,3S)-2,3-di-n-butoxycyclopentyl]maleimide, N-[(1S,2S,3S)-2,3-di-i-butoxycyclopentyl]maleimide, N-[(1S,2S,3S)-2,3-di-t-butoxycyclopentyl]maleimide, N-[(1S,2S,4S)-2,3-dimethylcyclopentyl]maleimide, N-[(1S,2S,4S)-2,3-diethylcyclopentyl]maleimide, N-[(1S,2S,4S)-2,3-di-n-propylcyclopentyl]maleimide, N-[(1S,2S,4S)-2,3-di-i-propylcyclopentyl]maleimide, N-[(1S,2S,4S)-2,3-di-n-butylcyclopentyl]maleimide, N-[(1S,2S,4S)-2,3-di-i-butylcyclopentyl]maleimide, N-[(1S,2S,4S)-2,3-di-t-butylcyclopentyl]maleimide, N-[(1S,2S,4S)-2,3-dimethoxycyclopentyl]maleimide, N-[(1S,2S,4S)-2,3-diethoxycyclopentyl]maleimide, N-[(1S,2S,4S)-2,3-di-n-propoxycyclopentyl]maleimide, N-[(1S,2S,4S)-2,3-di-i-propoxycyclopentyl]maleimide, N-[(1S,2S,4S)-2,3-di-n-butoxycyclopentyl]maleimide, N-[(1S,2S,4S)-2,3-di-i-butoxycyclopentyl]maleimide, N-[(1S,2S,4S)-2,3-di-t-butoxycyclopentyl]maleimide and the like.

Compounds having three or more substituents at any of the 2-, 3-, 4- and 5-positions of the cyclopentyl group include, for example, N-[(1S,2S,3S,4S)-2,3,4-trimethylcyclopentyl]maleimide, N-[(1S,2S,3S,4S)-2,3,4-triethylcyclopentyl]maleimide, N-[(1S,2S,3S,4S)-2,3,4-tri-n-propylcyclopentyl]maleimide, N-[(1S,2S,3S,4S)-2,3,4-tri-i-propylcyclopentyl]maleimide, N-[(1S,2S,3S,4S)-2,3,4-tri-n-butylcyclopentyl]maleimide, N-[(1S,2S,3S,4S)-2,3,4-tri-i-butylcyclopentyl]maleimide, N-[(1S,2S,3S,4S)-2,3,4-tri-t-butylcyclopentyl]maleimide, N-[(1S,2S,3S,4S)-2,3,4-trimethoxycyclopentyl]maleimide, N-[(1S,2S,3S,4S)-2,3,4-triethoxycyclopentyl]maleimide, N-[(1S,2S,3S,4S)-2,3,4-tri-n-propoxycyclopentyl]maleimide, N-[(1S,2S,3S,4S)-2,3,4-tri-i-propoxycyclopentyl]maleimide, N-[(1S,2S,3S,4S)-2,3,4-tri-n-butoxycyclopentyl]maleimide, N-[(1S,2S,3S,4S)-2,3,4-tri-i-butoxycyclopentyl]maleimide, N-[(1S,2S,3S,4S)-2,3,4-tri-t-butoxycyclopentyl]maleimide, N-[(1S,2S,3S,5S)-2,3,4-trimethylcyclopentyl]maleimide, N-[(1S,2S,3S,5S)-2,3,4-triethylcyclopentyl]maleimide, N-[(1S,2S,3S,5S)-2,3,4-tri-n-propylcyclopentyl]maleimide, N-[(1S,2S,3S,5S)-2,3,4-tri-i-propylcyclopentyl]maleimide, N-[(1S,2S,3S,5S)-2,3,4-tri-n-butylcyclopentyl]maleimide, N-[(1S,2S,3S,5S)-2,3,4-tri-i-butylcyclopentyl]maleimide, N-[(1S,2S,3S,5S)-2,3,4-tri-t-butylcyclopentyl]maleimide, N-[(1S,2S,3S,5S)-2,3,4-trimethoxycyclopentyl]maleimide, N-[(1S,2S,3S,5S)-2,3,4-triethoxycyclopentyl]maleimide, N-[(1S,2S,3S,5S)-2,3,4-tri-n-propoxycyclopentyl]maleimide, N-[(1S,2S,3S,5S)-2,3,4-tri-i-propoxycyclopentyl]maleimide, N-[(1S,2S,3S,5S)-2,3,4-tri-n-butoxycyclopentyl]maleimide, N-[(1S,2S,3S,5S)-2,3,4-tri-i-butoxycyclopentyl]maleimide, N-[(1S,2S,3S,5S)-2,3,4-tri-t-butoxycyclopentyl]maleimide, N-[(1S,2S,3S,4S,5R)-2,3,4,5-tetramethylcyclopentyl]maleimide, N-[(1S,2S,3S,4S,5S)-2,3,4,5-tetraethylcyclopentyl]maleimide, N-[(1S,2S,3S,4S,5S)-2,3,4,5-tetra-n-propylcyclopentyl]maleimide, N-[(1S,2S,3S,4S,5S)-2,3,4,5-tetra-i-propylcyclopentyl]maleimide, N-[(1S,2S,3S,4S,5S)-2,3,4,5-tetra-n-butylcyclopentyl]maleimide, N-[(1S,2S,3S,4S,5S)-2,3,4,5-tetra-i-butylcyclopentyl]maleimide, N-[(1S,2S,3S,4S,5S)-2,3,4,5-tetra-t-butylcyclopentyl]maleimide, N-[(1S,2S,3S,4S,5S)-2,3,4,5-tetramethoxycyclopentyl]maleimide, N-[(1S,2S,3S,4S,5S)-2,3,4,5-tetraethoxycyclopentyl]maleimide, N-[(1S,2S,3S,4S,5S)-2,3,4,5-tetra-n-propoxycyclopentyl]maleimide, N-[(1S,2S,3S,4S,5S)-2,3,4,5-tetra-i-propoxycyclopentyl]maleimide, N-[(1S,2S,3S,4S,5S)-2,3,4,5-tetra-n-butoxycyclopentyl]maleimide, N-[(1S,2S,3S,4S,5S)-2,3,4,5-tetra-i-butoxycyclopentyl]maleimide, N-[(1S,2S,3S,4S,5S)-2,3,4,5-tetra-t-butoxycyclopentyl]maleimide and the like. In the present invention, the optically active maleimide derivative represented by the above formula (1) includes not only these optically active compounds but also their emantiomers.

The optically active maleimide derivative represented by the above formula (1) is easily obtainable by reacting an optically active cyclopentylamine derivative represented by the above formula (2) with maleic acid.

Though there is no particular restriction on how to produce the optically active maleimide derivative represented by the above formula (1), the optically active maleimide derivative represented by the above formula (1) is obtainable, for example, by reacting an equimolar mixture of an optically active cyclopentylamine derivative represented by the above formula (2) and maleic anhydride in an inert solvent such as toluene in the presence of a dehydrator such as hexamethyldisilazane.

In the above formula (2), it is preferred that $R_3$—$X_3$, $R_4$—$X_4$, $R_5$—$X_5$ and $R_6$—$X_6$ are hydrogen atoms, each of $X_1$, $X_2$, $X_7$ and $X_8$ is independently a methylene group, an oxygen atom, a carbonyl group, a carbonyloxy group, a carbonylamino group, an aminocarbonyl group, an aminocarbonyloxy group or a single bond, and each of $R_1$, $R_2$, $R_7$ and $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group (provided that not all of $R_1$—$X_1$, $R_2$—$X_2$, $R_7$—$X_7$ and $R_8$—$X_8$ are the same substituents)

In the above formula (2), it is particularly preferred that $R_3$—$X_3$, $R_4$—$X_4$, $R_5$—$X_5$ and $R_6$—$X_6$ are hydrogen atoms, each of $X_1$, $X_2$, $X_7$ and $X_8$ is independently an oxygen atom or a single bond, and each of $R_1$, $R_2$, $R_7$ and $R_8$ is independently a hydrogen atom, a $C_{5-10}$ aromatic group, a benzyl group or a 2-phenylethyl group (provided that not all of $R_1$—$X_1$, $R_2$—$X_2$, $R_7$—$X_7$ and $R_8$—$X_8$ are the same substituents).

The optically active polymaleimide derivative of the present invention is a compound represented by the above formula (3).

In the above formula (3), it is preferred that $R_3$—$X_3$, $R_4$—$X_4$, $R_5$—$X_5$ and $R_6$—$X_6$ are hydrogen atoms, each of $X_1$, $X_2$, $X_7$ and $X_8$ is independently a methylene group, an oxygen atom, a carbonyl group, a carbonyloxy group, a carbonylamino group, an aminocarbonyl group, an aminocarbonyloxy group or a single bond, and each of $R_1$, $R_2$, $R_7$ and $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group (provided that not all of $R_1$—$X_1$, $R_2$—$X_2$, $R_7$—$X_7$ and $R_8$—$X_8$ are the same substituents).

In the above formula (3), it is particularly preferred that $R_3$—$X_3$, $R_4$—$X_4$, $R_5$—$X_5$ and $R_6$—$X_6$ are hydrogen atoms, each of $X_1$, $X_2$, $X_7$ and $X_8$ is independently an oxygen atom or a single bond, and each of $R_1$, $R_2$, $R_7$ and $R_8$ is independently a hydrogen atom, a $C_{5-10}$ aromatic group, a benzyl group or a 2-phenylethyl group (provided that not all of $R_1$—$X_1$, $R_2$—$X_2$, $R_7$—$X_7$ and $R_8$—$X_8$ are the same substituents).

As specific examples of the optically active polymaleimide derivative of the present invention represented by the above formula (3), compound having one substituent at the 2-, 3-, 4- or 5-position of the cyclopentyl group include, for example, poly{N-[(1S,2S)-2-methylcyclopentyl]maleimide}, poly{N-[(1S,2S)-2-ethylcyclopentyl]maleimide}, poly{N-[(1S,2S)-2-n-propylcyclopentyl]maleimide}, poly{N-[(1S,2S)-2-i-propylcyclopentyl]maleimide}, poly{N-[(1S,2S)-2-n-butylcyclopentyl]maleimide}, poly{N-[(1S,2S)-2-i-butylcyclopentyl]maleimide}, poly{N-[(1S,2S)-2-t-butylcyclopentyl]maleimide}, poly{N-[(1S,2S)-2-phenylcyclopentyl]maleimide}, poly{N-[(1S,2S)-2-benzylcyclopentyl]maleimide}, poly{N-[(1S,2S)-2-(2-phenylethyl)cyclopentyl]maleimide}, poly{N-[(1S,2S)-2-methoxycyclopentyl]maleimide}, poly{N-[(1S,2S)-2-ethoxycyclopentyl]maleimide}, poly{N-[(1S,2S)-2-n-propoxycyclopentyl]maleimide}, poly{N-[(1S,2S)-2-i-propoxycyclopentyl]maleimide}, poly{N-[(1S,2S)-2-n-butoxycyclopentyl]maleimide}, poly{N-[(1S,2S)-2-i-butoxycyclopentyl]maleimide}, poly{N-[(1S,2S)-2-t-butoxycyclopentyl]maleimide}, poly{N-[(1S,2S)-2-phenoxycyclopentyl]maleimide}, poly{N-[(1S,2S)-2-benzyloxycyclopentyl]maleimide}, poly{N-[(1S,2S)-2-(2-phenylethoxy)cyclopentyl]maleimide}, poly{N-[(1S,2S)-2-acetylcyclopentyl]maleimide}, poly{N-[(1S,2S)-2-propionylcyclopentyl]maleimide}, poly{N-[(1S,2S)-2-n-butyrylcyclopentyl]maleimide}, poly{N-[(1S,2S)-2-i-butyrylcyclopentyl]maleimide}, poly{N-[(1S,2S)-2-n-valerylcyclopentyl]maleimide}, poly{N-[(1S,2S)-2-i-valerylcyclopentyl]maleimide}, poly{N-[(1S,2S)-2-pivaloylcyclopentyl]maleimide}, poly{N-[(1S,2S)-2-benzoylcyclopentyl]maleimide}, poly{N-[(1S,2S)-2-phenylacetylcyclopentyl]maleimide}, poly{N-[(1S,2S)-2-

(3-phenylpropionyl)cyclopentyl]maleimide}, poly{N-[(1S,2S)-2-acetoxycyclopentyl]maleimide}, poly{N-[(1S,2S)-2-propionyloxycyclopentyl]maleimide}, poly{N-[(1S,2S)-2-n-butyryloxycyclopentyl]maleimide}, poly{N-[(1S,2S)-2-i-butyryloxycyclopentyl]maleimide}, poly{N-[(1S,2S)-2-n-valeryloxycyclopentyl]maleimide}, poly{N-[(1S,2S)-2-i-valeryloxycyclopentyl]maleimide}, poly{N-[(1S,2S)-2-pivaloyloxycyclopentyl]maleimide}, poly{N-[(1S,2S)-2-benzoyloxycyclopentyl]maleimide}, poly{N-[(1S,2S)-2-phenylacetoxycyclopentyl]maleimide}, poly{N-[(1S,2S)-2-(3-phenylpropionyloxy)cyclopentyl]maleimide}, poly{N-[(1S,2S)-2-methoxycarbonylcyclopentyl]maleimide}, poly{N-[(1S,2S)-2-ethoxycarbonylcyclopentyl]maleimide}, poly{N-[(1S,2S)-2-n-propoxycarbonylcyclopentyl]maleimide}, poly{N-[(1S,2S)-2-i-propoxycarbonylcyclopentyl]maleimide}, poly{N-[(1S,2S)-2-n-butoxycarbonylcyclopentyl]maleimide}, poly{N-[(1S,2S)-2-i-butoxycarbonylcyclopentyl]maleimide}, poly{N-[(1S,2S)-2-t-butoxycarbonylcyclopentyl]maleimide}, poly{N-[(1S,2S)-2-phenoxycarbonylcyclopentyl]maleimide}, poly{N-[(1S,2S)-2-benzyloxycarbonylcyclopentyl]maleimide}, poly{N-[(1S,2S)-2-(2-phenylethoxycarbonyl)cyclopentyl]maleimide}, poly{N-[(1S,2S)-2-N-acetylaminocyclopentyl]maleimide}, poly{N-[(1S,2S)-2-N-propionylaminocyclopentyl]maleimide}, poly{N-[(1S,2S)-2-N-n-butyrylaminocyclopentyl]maleimide}, poly{N-[(1S,2S)-2-N-i-butyrylaminocyclopentyl]maleimide}, poly{N-[(1S,2S)-2-N-n-valerylaminocyclopentyl]maleimide}, poly{N-[(1S,2S)-2-N-i-valerylaminocyclopentyl]maleimide}, poly{N-[(1S,2S)-2-N-pivaloylaminocyclopentyl]maleimide}, poly{N-[(1S,2S)-2-N-benzoylaminocyclopentyl]maleimide}, poly{N-[(1S,2S)-2-N-phenylacetylaminocyclopentyl]maleimide}, poly{N-[(1S,2S)-2-(N-3-phenylpropionylamino)cyclopentyl]maleimide}, poly{N-[(1S,2S)-2-N-methylcarbamoylcyclopentyl]maleimide}, poly{N-[(1S,2S)-2-N-ethylcarbamoylcyclopentyl]maleimide}, poly{N-[(1S,2S)-2-N-n-propylcarbamoylcyclopentyl]maleimide}, poly{N-[(1S,2S)-2-N-i-propylcarbamoylcyclopentyl]maleimide}, poly{N-[(1S,2S)-2-N-n-butylcarbamoylcyclopentyl]maleimide}, poly{N-[(1S,2S)-2-N-i-butylcarbamoylcyclopentyl]maleimide}, poly{N-[(1S,2S)-2-N-t-butylcarbamoylcyclopentyl]maleimide}, poly{N-[(1S,2S)-2-N-phenylcarbamoylcyclopentyl]maleimide}, poly{N-[(1S,2S)-2-N-benzylcarbamoylcyclopentyl]maleimide}, poly{N-[(1S,2S)-2-(N-2-phenylethylcarbamoyl)cyclopentyl]maleimide}, poly{N-[(1S,2S)-2-N-methylcarbamoyloxycyclopentyl]maleimide}, poly{N-[(1S,2S)-2-N-ethylcarbamoyloxycyclopentyl]maleimide}, poly{N-[(1S,2S)-2-N-n-propylcarbamoyloxycyclopentyl]maleimide}, poly{N-[(1S,2S)-2-N-i-propylcarbamoyloxycyclopentyl]maleimide}, poly{N-[(1S,2S)-2-N-n-butylcarbamoyloxycyclopentyl]maleimide}, poly{N-[(1S,2S)-2-N-i-butylcarbamoyloxycyclopentyl]maleimide}, poly{N-[(1S,2S)-2-N-t-butylcarbamoyloxycyclopentyl]maleimide}, poly{N-[(1S,2S)-2-N-phenylcarbamoyloxycyclopentyl]maleimide}, poly{N-[(1S,2S)-2-N-benzylcarbamoyloxycyclopentyl]maleimide}, poly{N-[(1S,2S)-2-(N-2-phenylethylcarbamoyloxy)cyclopentyl]maleimide} and the like.

Compounds having two substituents at any of the 2-, 3-, 4- and 5-positions of the cyclopentyl group include, for example, poly{N-[(1S,2S,3S)-2,3-dimethylcyclopentyl]maleimide}, poly{N-[(1S,2S,3S)-2,3-diethylcyclopentyl]maleimide}, poly{N-[(1S,2S,3S)-2,3-di-n-propylcyclopentyl]maleimide}, poly{N-[(1S,2S,3S)-2,3-di-i-propylcyclopentyl]maleimide}, poly{N-[(1S,2S,3S)-2,3-di-n-butylcyclopentyl]maleimide}, poly{N-[(1S,2S,3S)-2,3-di-i-butylcyclopentyl]maleimide}, poly{N-[(1S,2S,3S)-2,3-di-t-butylcyclopentyl]maleimide}, poly{N-[(1S,2S,3S)-2,3-dimethoxycyclopentyl]maleimide}, poly{N-[(1S,2S,3S)-2,3-diethoxycyclopentyl]maleimide}, poly{N-[(1S,2S,3S)-2,3-di-n-propoxycyclopentyl]maleimide}, poly{N-[(1S,2S,3S)-2,3-di-i-propoxycyclopentyl]maleimide}, poly{N-[(1S,2S,3S)-2,3-di-n-butoxycyclopentyl]maleimide}, poly{N-[(1S,2S,3S)-2,3-di-i-butoxycyclopentyl]maleimide}, poly{N-[(1S,2S,3S)-2,3-di-t-butoxycyclopentyl]maleimide}, poly{N-[(1S,2S,4S)-2,3-dimethylcyclopentyl]maleimide}, poly{N-[(1S,2S,4S)-2,3-diethylcyclopentyl]maleimide}, poly{N-[(1S,2S,4S)-2,3-di-n-propylcyclopentyl]maleimide}, poly{N-[(1S,2S,4S)-2,3-di-i-propylcyclopentyl]maleimide}, poly{N-[(1S,2S,4S)-2,3-di-n-butylcyclopentyl]maleimide}, poly{N-[(1S,2S,4S)-2,3-di-i-butylcyclopentyl]maleimide}, poly{N-[(1S,2S,4S)-2,3-di-t-butylcyclopentyl]maleimide}, poly{N-[(1S,2S,4S)-2,3-dimethoxycyclopentyl]maleimide}, poly{N-[(1S,2S,4S)-2,3-diethoxycyclopentyl]maleimide}, poly{N-[(1S,2S,4S)-2,3-di-n-propoxycyclopentyl]maleimide}, poly{N-[(1S,2S,4S)-2,3-di-i-propoxycyclopentyl]maleimide}, poly{N-[(1S,2S,4S)-2,3-di-n-butoxycyclopentyl]maleimide}, poly{N-[(1S,2S,4S)-2,3-di-i-butoxycyclopentyl]maleimide}, poly{N-[(1S,2S,4S)-2,3-di-t-butoxycyclopentyl]maleimide} and the like.

Compounds having three or more substituents at any of the 2-, 3-, 4- and 5-positions of the cyclopentyl group include, for example, poly{N-[(1S,2S,3S,4S)-2,3,4-trimethylcyclopentyl]maleimide}, poly{N-[(1S,2S,3S,4S)-2,3,4-triethylcyclopentyl]maleimide}, poly{N-[(1S,2S,3S,4S)-2,3,4-tri-n-propylcyclopentyl]maleimide}, poly{N-[(1S,2S,3S,4S)-2,3,4-tri-i-propylcyclopentyl]maleimide}, poly{N-[(1S,2S,3S,4S)-2,3,4-tri-n-butylcyclopentyl]maleimide}, poly{N-[(1S,2S,3S,4S)-2,3,4-tri-i-butylcyclopentyl]maleimide}, poly{N-[(1S,2S,3S,4S)-2,3,4-tri-t-butylcyclopentyl]maleimide}, poly{N-[(1S,2S,3S,4S)-2,3,4-trimethoxycyclopentyl]maleimide}, poly{N-[(1S,2S,3S,4S)-2,3,4-triethoxycyclopentyl]maleimide}, poly{N-[(1S,2S,3S,4S)-2,3,4-tri-n-propoxycyclopentyl]maleimide}, poly{N-[(1S,2S,3S,4S)-2,3,4-tri-i-propoxycyclopentyl]maleimide}, poly{N-[(1S,2S,3S,4S)-2,3,4-tri-n-butoxycyclopentyl]maleimide}, poly{N-[(1S,2S,3S,4S)-2,3,4-tri-i-butoxycyclopentyl]maleimide}, poly{N-[(1S,2S,3S,4S)-2,3,4-tri-t-butoxycyclopentyl]maleimide}, poly{N-[(1S,2S,3S,5S)-2,3,4-trimethylcyclopentyl]maleimide}, poly{N-[(1S,2S,3S,5S)-2,3,4-triethylcyclopentyl]maleimide}, poly{N-[(1S,2S,3S,5S)-2,3,4-tri-n-propylcyclopentyl]maleimide}, poly{N-[(1S,2S,3S,5S)-2,3,4-tri-i-propylcyclopentyl]maleimide}, poly{N-[(1S,2S,3S,5S)-2,3,4-tri-n-butylcyclopentyl]maleimide}, poly{N-[(1S,2S,3S,5S)-2,3,4-tri-i-butylcyclopentyl]maleimide}, poly{N-[(1S,2S,3S,5S)-2,3,4-tri-t-butylcyclopentyl]maleimide}, poly{N-[(1S,2S,3S,5S)-2,3,4-trimethoxycyclopentyl]maleimide}, poly{N-[(1S,2S,3S,5S)-2,3,4-triethoxycyclopentyl]maleimide}, poly{N-[(1S,2S,3S,5S)-2,3,4-tri-n-propoxycyclopentyl]maleimide}, poly{N-[(1S,2S,3S,5S)-2,3,4-tri-i-propoxycyclopentyl]maleimide}, poly{N-[(1S,2S,3S,5S)-2,3,4-tri-n-butoxycyclopentyl]maleimide}, poly{N-[(1S,2S,3S,5S)-2,3,4-tri-i-butoxycyclopentyl]maleimide}, poly{N-[(1S,2S,3S,5S)-2,3,4-tri-t-butoxycyclopentyl]maleimide}, poly{N-[(1S,2S,3S,4S,5R)-2,3,4,5-tetramethylcyclopentyl]maleimide}, poly{N-[(1S,2S,3S,4S,5S)-2,3,4,5-tetraethylcyclopentyl]maleimide}, poly{N-[(1S,2S,3S,4S,5S)-2,3,4,5-tetra-n-propylcyclopentyl]maleimide}, poly{N-[(1S,2S,3S,4S,5S)-2,3,4,5-tetra-i-propylcyclopentyl]maleimide}, poly{N-[(1S,2S,3S,4S,5S)-2,3,4,5-tetra-n-butylcyclopentyl]maleimide}, poly{N-[(1S,2S,3S,4S,5S)-2,3,4,5-tetra-i-butylcyclopentyl] maleimide}, poly{N-[(1S,2S,3S,4S,5S)-2,3,4,5-tetra-t-butylcyclopentyl]maleimide}, poly{N-[(1S,2S,3S,4S,5S)-2,3,4,5-tetramethoxycyclopentyl]maleimide}, poly{N-[(1S,2S,3S,4S,5S)-2,3,4,5-tetraethoxycyclopentyl]maleimide}, poly{N-[(1S,2S,3S,4S,5S)-2,3,4,5-tetra-n-propoxycyclopentyl]maleimide}, poly{N-[(1S,2S,3S,4S,5S)-2,3,4,5-tetra-i-propoxycyclopentyl]maleimide}, poly{N-[(1S,2S,3S,4S,5S)-2,3,4,5-tetra-n-butoxycyclopentyl]maleimide}, poly{N-[(1S,2S,3S,4S,5S)-2,3,4,5-tetra-i-butoxycyclopentyl]maleimide}, poly{N-[(1S,2S,3S,4S,5S)-2,3,4,5-tetra-t-butoxycyclopentyl]maleimide} and the like. In the present invention, the optically active polymaleimide derivative represented by the above formula (3) includes not only these optically active compounds but also polymers obtained by asymmetric anionic polymerization of their emantiomers as the monomers.

The optically active polymaleimide derivative of the present invention represented by the above formula (3) is obtainable by asymmetric anionic polymerization of the optically active maleimide derivative represented by the above formula (1).

In the present invention, though there is no restriction on the polymerization method, the reaction is carried out, for example, by adding the optically active maleimide derivative as the starting material to a solution of an asymmetric ligand and an anionic polymerization catalyst in the reaction solvent.

In the present invention, the anionic polymerization catalyst may, for example, be an organic metal catalyst such as n-butyllithium, fluorenyllithium, diethylzinc and dimethylzinc and is used usually in an amount of from 0.1 to 30 mol %, based on the optically active maleimide derivative as the starting material to be subjected to the reaction.

In the present invention, though the optically active ligand used in the anionic polymerization is not particularly limited, it is preferably a bisoxazoline derivative represented by the following formula (4):

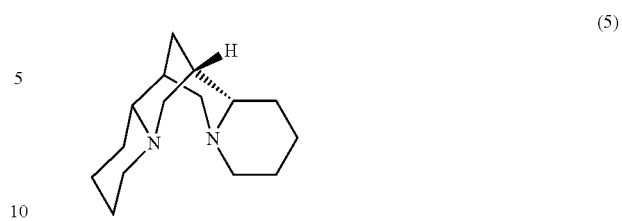

wherein $R_1$ is a methyl group, an ethyl group, a $C_{3-8}$ linear, branched or cyclic saturated or unsaturated hydrocarbon group, a $C_{6-20}$ aryl group or a $C_{6-20}$ alkyl group substituted with at least one substituent selected from the group consisting of a methyl group, an ethyl group, a $C_{3-8}$ linear, branched or cyclic saturated or unsaturated hydrocarbon group and a $C_{6-20}$ aryl group, B is a $C_{0-5}$ methylene group, C is a $C_{1-10}$ alkylidene group or an aryl group, and * indicates optically active carbon, or a (−)-sparteine (hereinafter referred to as Sp) represented by the following formula (5).

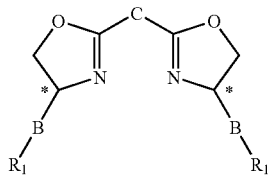

As the bisoxazoline derivative represented by the above formula (4), (4S)-2,2'-(1-ethylpropylidene)bis[4-(1-phenylethyl)-4,5-dihydroxazole], (4S)-2,2'-(1-ethylpropylidene)bis[4-(1-(1-naphthyl) ethyl)-4,5-dihydroxazole], (4S)-2,2'-(1-methylethylidene)bis[4-(1-phenylethyl)-4,5-dihydroxazole], (4S)-2,2'-(cyclopropylidene)bis[4-(1-phenylethyl)-4,5-dihydroxazole], (4S)-2,2'-(1,3-phenyl)bis [4-(1-phenylethyl)-4,5-dihydroxazole], (4S)-2,2'-(2,6-pyridyl)bis[4-(1-phenylethyl)-4,5-dihydroxazole] or the like may be specifically mentioned.

In the present invention, such an optically active ligand is used theoretically in an equimolar amount with the anionic polymerization catalyst to be used for the reaction, but it is used preferably in an amount of from 1.02 to 1.5 moles, to carry out the reaction stably.

The solvent used for the asymmetric anionic polymerization may be any solvent inert to the reaction without any particular restrictions, and an ethereal solvent such as diethyl ether, di-n-propyl ether, di-i-propyl ether, di-n-butyl ether, di-t-butyl ether, tetrahydrofuran (hereinafter referred to simply as THF) or an aromatic hydrocarbon solvent such as benzene, toluene, xylene, ethylbenzene or mesitylene may be specifically mentioned.

In the present invention, the amount of the solvent used for the asymmetric anionic polymerization is not particularly limited, and it is used usually in an amount of from 2 to 100 times by weight that of the optically active maleimide derivative to be subjected to the reaction.

In the present invention, the reaction temperature for the asymmetric anionic polymerization varies depending on the reaction conditions and is not particularly limited, but the reaction is usually carried out at −78 to 100° C.

In the present invention, the reaction time for the asymmetric anionic polymerization depends on the catalyst and the reaction temperature and is not particularly limited, but the reaction is usually completed within from 1 to 336 hours.

After the polymerization reaction, the reaction solution is added dropwise to a solvent in which the product has a low solubility such as hexane, heptane, methanol, ethanol or isopropanol to crystallize the optically active polymaleimide derivative of the present invention represented by the above formula (3) as powder. In the present invention, to improve the purity, it may be dissolved again in a solvent such as THF or toluene and recrystallized from a solvent such as methanol.

The separating medium of the present invention comprises the optically active polymaleimide derivative represented by the above formula (3) and can be used widely as a separating medium for optically active substances.

Specifically, the separating medium of the present invention is made of the optically active polymaleimide derivative represented by the above formula (3) itself or comprises the optically active polymaleimide derivative represented by the above formula (3) and a carrier supporting the optically active polymaleimide derivative.

In the separating medium of the present invention, though the carrier is not particularly limited, silica gel, alumina, crosslinked polystyrene, a polyacrylic acid derivative or polysiloxane with or without alkylsilane surface treatment may be mentioned. Among them, carriers having a particle size of from 1 μm to 200 μm and an average pore size of from 10 to 3000 Å are preferable for separating media for high performance liquid chromatography or gas chromatography.

In the separating medium of the present invention, the optically active polymaleimide derivative may be supported by the carrier by any means without any particular restrictions and may be supported physically by bringing the optically active polymaleimide derivative into contact with the carrier or by preparing the optically active polymaleimide derivative with a terminal functional group and forming a chemical bond with the carrier.

In the separating medium of the present invention, the amount of the optically active polymaleimide derivative represented by the above formula (3) to be supported on the carrier depends on the kind and physical properties of the carrier to be used and is not particularly limited, but it is usually within the range of from 1 to 50 wt %, based on the weight of the filler.

The separating medium of the present invention comprising the optically active polymaleimide derivative represented by the above formula (3) and a carrier supporting the optically active polymaleimide derivative can be used for separation of numbers of the optically active compounds. For example, a glass or metal column packed with the separating medium of the present invention may be used as a packed column for chromatography. For example, as a packed column for high performance liquid chromatography, it is widely applicable to both normal phase liquid chromatography using hexane-isopropanol or the like as the eluent and reverse phase liquid chromatography using alcohol-water or the like as the eluent.

There is not restriction on how to separate optically active substances by using the separating medium of the present invention, and optically active substances are easily separated, for example, by high performance liquid chromatography or gas chromatography. The separating medium of the present invention can be used as a shifting reagent for nuclear magnetic resonance spectroscopy (hereinafter referred to simply as NMR).

The present invention provides a novel optically active maleimide derivative and a novel optically active polymaleimide derivative. The separating medium comprising the optically active polymaleimide derivative of the present invention is extremely useful as a separating medium for optical resolution.

Now, the present invention will be described in further detail with reference to Examples. However, it should be understood that the present invention is by no means restricted to such specific Examples.

The average molecular weight was measured by gel permeation chromatography (high performance GPC system, manufactured by TOSOH CORPORATION) and calculated as a standard polystyrene, the angle of rotation was measured with SEPA-300, manufactured by HORIBA, the MASS spectra were measured with M-80B, manufactured by Hitachi, Ltd., the $^1$H-NMR and $^{13}$C-NMR spectra were measured with Gemini-200, manufactured by Varian, and the IR spectra were measured with 2000FT-IR, manufactured by Perkin Elmer.

For the measurement of the resolution power of the optically active polymaleimide derivatives prepared, a multiple pump CCPM, manufactured by TOSOH CORPORATION, an ultraviolet detector UV-8020 and an integrator CHROMATOCORDER 21 were used.

EXAMPLE 1

Preparation of
N-[(1S,2S)-2-benzyloxycyclopentyl]maleimide 2.55 g (26.0 mmol) of maleic anhydride and 140 ml of dry benzene were put into a 500 ml three-neck round-bottom flask equipped with a condenser, a dropping funnel and a stirrer, dissolved with stirring and then cooled to 0° C. on an ice bath.

Then, 4.97 g (26.0 mmol) of (1S,2S)-2-benzyloxycyclopentylamine in 80 ml of dry benzene was added through the dropping funnel, and the mixture was returned to room temperature and stirred for 1 hour.

Further, the reaction solution was stirred vigorously with 3.54 g (26.0 mmol) of zinc chloride and then heated to 80° C. on an oil bath. 8.39 g (52.0 mmol) of hexamethyldisilazane in 70 ml of dry benzene was added dropwise through the dropping funnel, and the reaction was carried out for 5 hours under reflux by heating.

After completion of the reaction, the reaction solution was cooled to room temperature, washed with 2N hydrochloric acid and extracted with ethyl acetate, and the extract was washed with saturated aqueous sodium hydrogencarbonate, saturated aqueous sodium chloride dried over anhydrous magnesium sulfate and concentrated to give crude N-[(1S,2S)-2-benzyloxycyclopentyl]maleimide. Purification of the N-[(1S,2S)-2-benzyloxycyclopentyl]maleimide thus obtained by column chromatography (n-hexane/ethyl acetate=9/1, vol/vol) gave 6.40 g of a pale yellow oil (yield 91%).

Specific rotation $[\alpha]_D^{25}$=+36.6° (C=1.0, THF, 1=10 cm)
$^1$H-NMR (CDCl$_3$) σ7.32-7.21 (m,5H), 6.61 (s,2H), 4.51-4.25 (m,4H), 2.20-1.63 (m,6H)
$^{13}$C-NMR (CDCl$_3$) σ170.39, 138.29, 133.77, 128.13, 127.34, 127.30, 81.62, 71.20, 56.66, 30.97, 27.82, 21.94
MASS (m/z) 272 ([M+H]$^+$)
IR (KBr: γ cm$^{-1}$) 3099, 3065, 3031, 2962, 2874, 1768, 1705, 1595, 1496, 1454, 1404, 1203, 1176, 1140, 1027, 913, 827, 738, 696
Anal.: C70.69, H6.31, N5.04 (Calc.: C70.83, H6.32, N5.16).

EXAMPLE 2

Preparation of
N-[(1R,2R)-2-benzyloxycyclopentyl]maleimide 2.55 g (26.0 mmol) of maleic anhydride and 140 ml of dry benzene were put into a 500 ml three-necked round-bottom flask equipped with a condenser, a dropping funnel and a stirrer, dissolved with stirring and then cooled to 0° C. on an ice bath.

Then, 4.97 g (26.0 mmol) of (1R,2R)-2-benzyloxycyclopentylamine in 80 ml of dry benzene was added through the dropping funnel, and the mixture was returned to room temperature and stirred for 1 hour.

Further, the reaction solution was stirred vigorously with 3.54 g (26.0 mmol) of zinc chloride and then heated to 80° C. on an oil bath. 8.39 g (52.0 mmol) of hexamethyldisilazane in 70 ml of dry benzene was added dropwise through the dropping funnel, and the reaction was carried out for 5 hours under reflux by heating.

After completion of the reaction, the reaction solution was cooled to room temperature, washed with 2N hydrochloric acid and extracted with ethyl acetate, and the extract was washed with saturated aqueous sodium hydrogencarbonate, saturated aqueous sodium chloride dried over anhydrous magnesium sulfate and concentrated to give crude N-[(1R, 2R)-2-benzyloxycyclopentyl]maleimide. Purification of the N-[(1R,2R)-2-benzyloxycyclopentyl]maleimide thus obtained by column chromatography (n-hexane/ethyl acetate=9/1, vol/vol) gave 6.73 g of a pale yellow oil (yield 96%).

Specific rotation $[\alpha]_D^{25}$=−36.6° (C=1.0, THF, 1=10 cm)

$^1$H-NMR (CDCl$_3$) σ7.32-7.21 (m,5H), 6.61 (s,2H), 4.51-4.25 (m, 4H), 2.20-1.63 (m,6H)

$^{13}$C-NMR (CDCl$^3$) σ170.39, 138.29, 133.77, 128.13, 127.34, 127.30, 81.62, 71.20, 56.66, 30.97, 27.82, 21.94

MASS (m/z) 272 ([M+H]$^+$)

IR (KBr: γ cm$^{-1}$) 3099, 3065, 3031, 2962, 2874, 1768, 1705, 1595, 1496, 1454, 1404, 1203, 1176, 1140, 1027, 913, 827, 738, 696

Anal.: C70.72, H6.27, N5.18 (Calc.: C70.83, H6.32, N5.16).

EXAMPLE 3

Preparation of optically active poly{N-[(1S,2S)-2-benzyloxycyclopentyl]maleimide}

0.12 g (1.0 mmol) of diethylzine, 0.28 g (1.2 mmol) of (−)-sparteine and 2 ml of dry toluene were put into a 50 ml eggplant type flask with a magnetic stirrer inside and stirred at −10° C. for 30 minutes. The resulting solution was added to 2.71 g (10.0 mmol) of N-[(1S,2S)-2-benzyloxycyclopentyl]maleimide obtained in Example 1 in 18 ml of dry toluene, and the reaction was carried out at the same temperature for 168 hours.

After completion of the reaction, the reaction solution was poured into 200 ml of methanol, and the precipitate was collected by filtration. The red solid was washed with 1N hydrochloric acid and with water and dried at room temperature under reduced pressure to give 2.23 g of the desired optically active poly{N-[(1S,2S)-2-benzyloxycyclopentyl]maleimide} as a white solid (yield 82%).

Number average molecular weight (Mn)=20.5×10$^3$, Mw/Mn=7.0

Specific rotation $[\alpha]_{435}^{25}$=209.6° (C=1.0, CHCl$_3$)

$^1$H-NMR (CDCl$_3$) σ7.35 (br,5H), 4.50-4.02 (br,4H), 2.04-1.74 (br,6H)

$^{13}$C-NMR(CDCl$_3$) σ176.27, 138.24, 128.28, 127.78, 127.44, 82.96, 71.38, 58.35, 43.48, 32.45, 28.13, 23.41

IR (KBr: γ cm$^{-1}$) 3063, 3031, 2960, 2876, 1773, 1686, 1496, 1454, 1395, 1212, 1152, 1095, 1028, 911, 847, 815, 738, 697, 646

Anal.: C71.02, H6.24, N5.29 (Calc.: C70.83, H6.32, N5.16).

EXAMPLE 4

Preparation of optically active poly{N-[(1R,2R)-2-benzyloxycyclopentyl]maleimide}

0.12 g (1.0 mmol) of diethylzine, 0.28 g (1.2 mmol) of (−)-sparteine and 2 ml of dry toluene were put into a 50 ml eggplant type flask with a magnetic stirrer inside and stirred at −10° C. for 30 minutes. The resulting solution was added to 2.71 g (10.0 mmol) of N-[(1R,2R)-2-benzyloxycyclopentyl]maleimide obtained in Example 2 in 18 ml of dry toluene, and the reaction was carried out at the same temperature for 168 hours.

After completion of the reaction, the reaction solution was poured into 200 ml of methanol, and the precipitate was collected by filtration. The red solid was washed with 1N hydrochloric acid and with water and dried at room temperature under reduced pressure to give 2.23 g of the desired optically active poly{N-[(1S,2S)-2-benzyloxycyclopentyl]maleimide} as a white solid (yield 66%).

Number average molecular weight (Mn)=19.1×10$^3$, Mw/Mn=7.1

Specific rotation $[\alpha]_{435}^{25}$=37.9° (C=1.0, CHCl$_3$)

$^1$H-NMR (CDCl$_3$) σ7.35 (br,5H), 4.50-4.02 (br,4H), 2.04-1.74 (br,6H)

$^{13}$C-NMR (CDCl$_3$) σ176.27, 138.24, 128.28, 127.78, 127.44, 82.96, 71.38, 58.35, 43.48, 32.45, 28.13, 23.41

IR (KBr: γ cm$^{-1}$) 3063, 3031, 2961, 2874, 1773, 1692, 1496, 1454, 1397, 1212, 1152, 1097, 1028, 911, 847, 815, 739, 697, 646

Anal.: C70.74, H6.47, N5.10 (Calc.: C70.83, H6.32, N5.16).

EXAMPLE 5

Preparation of 10% optically active poly{N-[(1S, 2S)-2-benzyloxycyclopentyl]maleimide}-Supporting Silica Gel and a Column Packed Therewith 500 mg of the optically active poly{N-[(1S,2S)-2-benzyloxycyclopentyl]maleimide} obtained in Example 2 was dissolved in and 10 ml of chloroform in a 50 ml eggplant type flask and dissolved, and 4.5 g of silica gel (average particle size 5 μm, average pore size 100 Å) was added. Then, the chloroform was distilled off under reduced pressure by means of a rotary evaporator to give 5 g of the desired 10% optically active poly{N-[(1S,2S)-2-benzyloxycyclopentyl]maleimide}-loaded silica gel.

The 10% optically active poly{N-[(1S,2S)-2-benzyloxycyclopentyl]maleimide}-supporting silica gel was dispersed in isopropanol and packed into a stainless steel column of 4.6 mmID×150 mmL by means of a high pressure pump under a pressure of 300 kg/cm$^2$. The theoretical plate number of the packed column was 4470.

The theoretical plate number was measured by eluting toluene with n-hexane/isopropanol=90/10 (vol/vol) as the eluent and calculated by the following formula.

Theoretical plate number $(N)$=5.54×$\{Tr/W_{1/2}\}^2$

Tr=retention time (sec)

$W_{1/2}$=half value width (mm)

EXAMPLES 6 to 9

Various compounds were separated by using the column prepared in Example 5 under the conditions shown in Table 1. The results are shown in Table 1.

TABLE 1

| Example | Compound[1] | Mobile phase[2] | Flow rate ml/min | k1[3] | k2[4] | α[5] |
|---|---|---|---|---|---|---|
| 6 | A | (1) | 1.0 | 0.95 | 1.08 | 1.14 |
| 7 | B | (1) | 1.0 | 0.74 | 1.45 | 1.97 |

TABLE 1-continued

| Example | Compound[1] | Mobile phase[2] | Flow rate ml/min | k1'[3] | k2'[4] | α[5] |
|---|---|---|---|---|---|---|
| 8 | C | (1) | 1.0 | 0.40 | 0.50 | 1.23 |
| 9 | D | (1) | 1.0 | 4.34 | 4.74 | 1.09 |

[1])Compound A: 2-methyl-1-tetralone
Compound B: benzoin
Compound C: methyl 2-chloropropionate
Compound D: 2-benzyloxymethyl-2,3-dihydro-4H-pyran-4-one
[2])Mobile phase (1): n-hexane/isopropanol = 90/10 (vol/vol)
[3])k1': Retention coefficient of the first eluted enantiomer
k1' = (t1 − t0)/t0
(as t0, the value of 1,3,5-tri-tert-butylbenzene was used)
[4])k2': Retention coefficient of the second eluted enantiomer
k2' = (t2 − t0)/t0 (as t0, the value of 1,3,5-tri-tert-butylbenzene was used)
[5])α: Separation factor
α = k2'/k1'

The entire disclosure of Japanese Patent Application No. 2003-144793 filed on May 22, 2003 including specification, claims and summary is incorporated herein by reference in its entirety.

What is claimed is:

1. An optically active polymaleimide compound represented by the following formula (3):

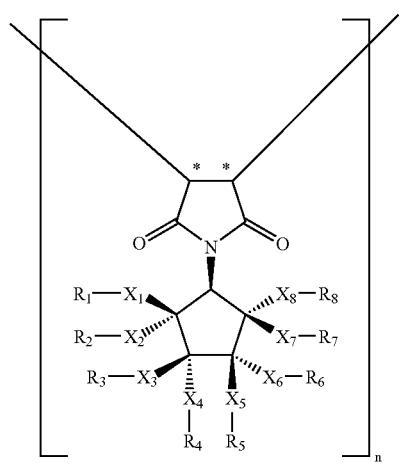

(3)

wherein each of $X_1$ to $X_8$ is independently a methylene group, an oxygen atom, a carbonyl group, a carbonyloxy group, a carbonylamino group, an aminocarbonyl group, an aminocarbonyloxy group or a single bond, each of $R_1$ to $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group, provided that not all of $R_1$—$X_1$, $R_2$—$X_2$, $R_3$—$X_3$, $R_4$—$X_4$, $R_5$—$X_5$, $R_6$—$X_6$, $R_7$—$X_7$ and $R_8$—$X_8$ are the same substituents, n is from 2 to 10000, and * indicates asymmetric carbon.

2. The optically active polymaleimide compound according to claim 1, wherein in the formula (3), $R_3$—$X_3$, $R_4$—$X_4$, $R_5$—$X_5$ and $R_6$—$X_6$ are hydrogen atoms, each of $X_1$, $X_2$, $X_7$ and $X_8$ is independently a methylene group, an oxygen atom, a carbonyl group, a carbonyloxy group, a carbonylamino group, an aminocarbonyl group, an aminocarbonyloxy group or a single bond, and each of $R_1$, $R_2$, $R_7$ and $R_8$ is independently a hydrogen atom, a methyl group, an ethyl group, a $C_{3-10}$ linear, branched or cyclic alkyl group, a methoxy group, an ethoxy group, a $C_{3-10}$ linear, branched or cyclic alkoxy group, a $C_{5-10}$ aromatic group, a $C_{5-10}$ aromatic group having 1 to 4 methyl groups on the aromatic group instead of hydrogen, a $C_{5-10}$ aromatic group having 1 to 4 ethyl groups on the aromatic group instead of hydrogen, a $C_{5-10}$ aromatic group having 1 to 4 $C_{3-6}$ linear, branched or cyclic alkyl groups on the aromatic group instead of hydrogen, a $C_{5-10}$ aromatic group having 1 to 4 methoxy groups on the aromatic group instead of hydrogen, a $C_{5-10}$ aromatic group having 1 to 4 ethoxy groups on the aromatic group instead of hydrogen, a $C_{5-10}$ aromatic group having 1 to 4 $C_{3-6}$ linear, branched or cyclic alkoxy groups on the aromatic group instead of hydrogen, a benzyl group, a benzyl group having 1 to 4 methyl groups on the aromatic group instead of hydrogen, a benzyl group having 1 to 4 ethyl groups on the aromatic group instead of hydrogen, a benzyl group having 1 to 4 $C_{3-6}$ linear, branched or cyclic alkyl groups on the aromatic group instead of hydrogen, a benzyl group having 1 to 4 methoxy groups on the aromatic group instead of hydrogen, a benzyl group having 1 to 4 ethoxy groups on the aromatic group instead of hydrogen, a benzyl group having 1 to 4 $C_{3-6}$ linear, branched or cyclic alkoxy groups on the aromatic group instead of hydrogen, a 2-phenylethyl group, a 2-phenylethyl group having 1 to 4 methyl groups on the aromatic group instead of hydrogen, a 2-phenylethyl group having 1 to 4 ethyl groups on the aromatic group instead of hydrogen, a 2-phenylethyl group having 1 to 4 $C_{3-6}$ linear, branched or cyclic alkyl groups on the aromatic group instead of hydrogen, a 2-phenylethyl group having 1 to 4 methoxy groups on the aromatic group instead of hydrogen, a 2-phenylethyl group having 1 to 4 ethoxy groups on the aromatic group instead of hydrogen, a 2-phenylethyl group having 1 to 4 $C_{3-6}$ linear, branched or cyclic alkoxy groups on the aromatic group instead of hydrogen or a 5 to 10-membered heterocyclic aromatic group (provided that not all of $R_1$—$X_1$, $R_2$—$X_2$, $R_7$—$X_7$ and $R_8$-$X_8$ are the same substituents).

3. The optically active polymaleimide compound according to claim 1, wherein in the formula (3), $R_3$—$X_3$, $R_4$—$X_4$, $R_5$—$X_5$ and $R_6$-$X_6$ are hydrogen atoms, each of $R_1$—$X_1$, $R_2$—$X_2$, $R_7$—$X_7$ and $R_8$-$X_8$ is independently an oxygen atom or a single bond, and each of $R_1$, $R_2$, $R_7$ and $R_8$ is independently a hydrogen atom, a $C_{5-10}$ aromatic group, a benzyl group or a 2-phenylethyl group (provided that not all of $R_1$—$X_1$, $R_2$—$X_2$, $R_7$—$X_7$ and $R_8$-$X_8$ are the same substituents).

4. The optically active polymaleimide compound according to claim 1, wherein in the formula (3), $R_3$—$X_3$, $R_4$—$X_4$, $R_5$—$X_5$ and $R_6$—$X6$ are hydrogen atoms, each of $X_1$, $X_2$, $X_7$ and $X_8$ is independently a hydrogen atom or a benzyloxy group (provided that not all of $R_1$—$X_1$, $R_2$—$X_2$, $R_7$—$X_7$ and $R_8$—$X_8$ are the same substituents).

5. A process for producing the optically active polymaleimide compound according to claim 1, which comprises asymmetric anionic polymerization of the optically active maleimide compound as defined formula (1).

6. The process according to claim 5, wherein the asymmetric anionic polymerization is carried out in the presence of an asymmetric ligand represented by the following formula (4):

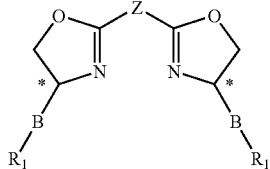

(4)

wherein $R_1$ is a methyl group, an ethyl group, a $C_{3-8}$ linear, branched or cyclic saturated or unsaturated hydrocarbon group, a $C_{6-20}$ aryl group or a $C_{20}$ alkyl group substituted with at least one substituent selected from the group consisting of a methyl group, an ethyl group, a $C_{3-8}$ linear, branched or cyclic saturated or unsaturated hydrocarbon group and a $C_{6-20}$ aryl group, B is a single bond or a $C_{1-5}$ methylene group, and Z is a $C_{1-10}$ alkylidene group or an aryl group, and * indicates an optically active carbon, or the following formula (5)

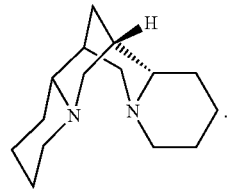

(5)

* * * * *